US00PP30583P2

(12) United States Plant Patent
Egger

(10) Patent No.: US PP30,583 P2
(45) Date of Patent: Jun. 18, 2019

(54) ***HEUCHERA* PLANT NAMED 'TNHEUNEB'**

(50) Latin Name: ***Heuchera* hybrid**
Varietal Denomination: TNHEUNEB

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,794

(22) Filed: Apr. 25, 2018

(51) Int. Cl.
*A01H 5/02* (2018.01)
*A01H 6/80* (2018.01)

(52) U.S. Cl.
USPC ..... Plt./440
CPC ..... *A01H 6/80* (2018.05); *A01H 5/02* (2013.01)

(58) Field of Classification Search
USPC ..... Plt./440
CPC ..... A01H 5/02
See application file for complete search history.

(56) References Cited

PUBLICATIONS https://www.greenhousegrower.com/varieties/terra-nova-adds-two-new-heuchera-to-its-northern-exposure-series/; Jan. 18, 2018; 8 pages.*

* cited by examiner

*Primary Examiner* — Kent L Bell
(74) *Attorney, Agent, or Firm* — Klarquist Sparkman, LLP

(57) ABSTRACT

A new and distinct *Heuchera* plant characterized by brown-black to black colored leaves, medium large, geranium-like leaves, very light pink flowers on upright flowering stems, good cold and sun tolerance, a large, mounding habit with excellent crown count, and excellent vigor.

1 Drawing Sheet

Botanical denomination: *Heuchera* hybrid.
Variety designation: 'TNHEUNEB'.

BACKGROUND OF THE INVENTION

The present invention relates to a new and distinct cultivar of *Heuchera* and given the cultivar name of 'TNHEUNEB'. *Heuchera* is in the family Saxifragaceae. *Heuchera* 'TNHEUNEB' originated from a controlled cross using *Heuchera* 'K963-1', a proprietary, unpatented, plant as the seed parent, and *Heuchera* 'K991-2', a proprietary, unpatented, plant as the pollen parent. These parents are a result of breeding using hardy *Heuchera richardsonii* with proprietary hybrid lines. *Heuchera* 'TNHEUNEB' was bred to be a hardy, large, landscape plant.

The trademark designation for the claimed plant is Northern Exposure™ Black.

Compared to the seed parent, *Heuchera* 'K963-1', the new cultivar has larger, blacker leaves, and a larger habit.

Compared to the pollen parent, *Heuchera* 'K991-2', the new cultivar has a larger habit and shinier black leaves.

Compared to *Heuchera* 'Obsidian', U.S. Plant Pat. No. 14,836, the new cultivar has larger, rounder leaves and a bigger habit.

Compared to *Heuchera* 'Blackout', U.S. Plant Pat. No. 20,613, the new cultivar has larger leaves with more rounded leaf lobes, and a bigger habit.

This new *Heuchera* is uniquely distinguished by:

1. brown-black to black colored leaves,
2. medium large, geranium-like leaves with shallow rounded lobes,
3. very light pink flowers on upright flowering stems, 4. good cold and sun tolerance,
5. a large, mounding habit with an excellent crown count, and
6. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
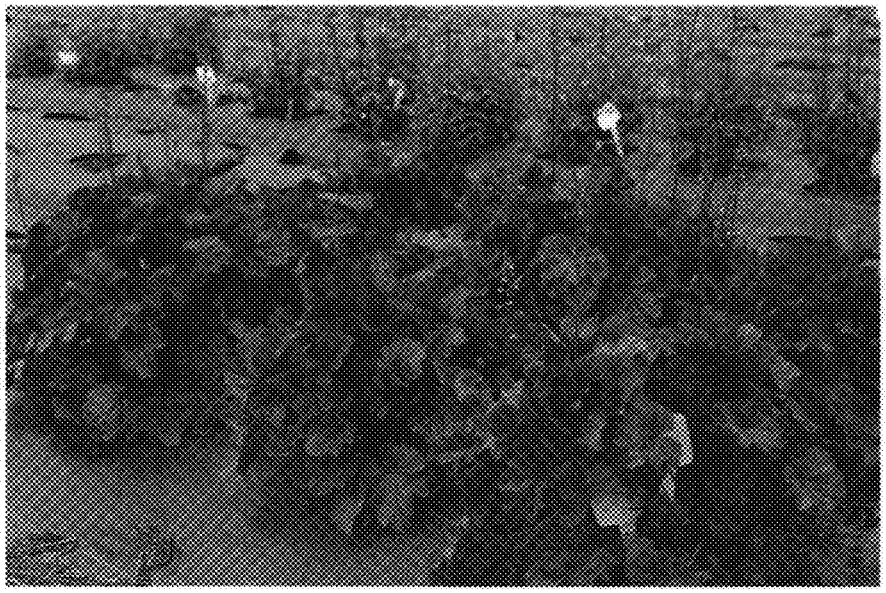
FIG. 1 shows a three-year-old plant of *Heuchera* 'TNHEUNEB' growing in the trial bed in partial shade in May in Canby, Oreg.
Figure 2:
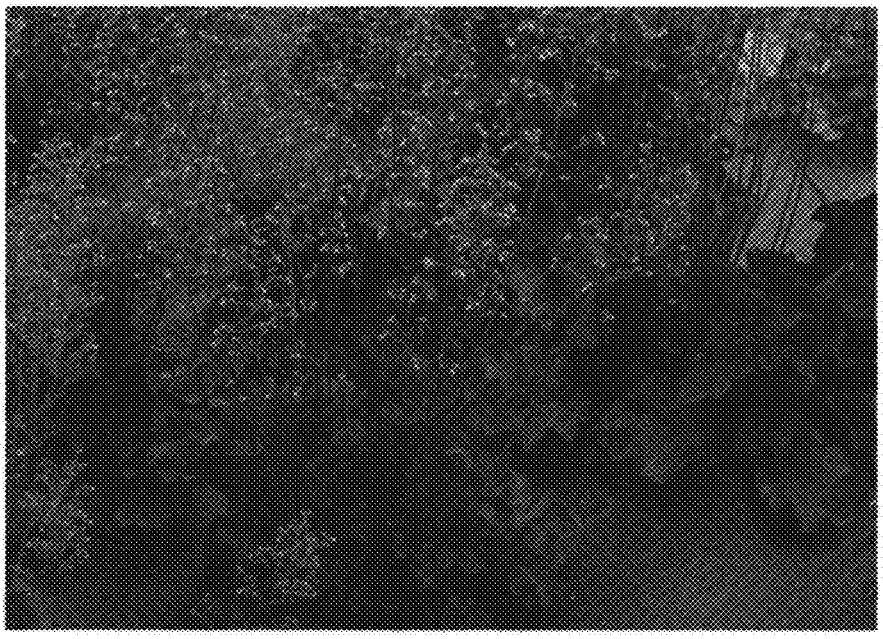
FIG. 2 shows one-year-old plants of the new cultivar in August in the trial beds in full sun in Canby, Oreg.

The following is a detailed description of the new *Heuchera* cultivar based on observations taken in August of three-year-old specimens growing in the trial field in part shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5th edition, 2007.

Plant:

*Form*.—Basal rosette, herbaceous perennial.

*Hardiness*.—USDA Zone 4 to 9.

*Size*.—20 cm tall from top of the foliage to the ground, up to 76 cm tall from top of flowers to the ground and 60 cm wide.

*Number of crowns*.—About 25.

*Habit*.—Medium large, mounding.

*Vigor*.—Excellent.

Leaf:

*Type*.—Simple.

*Arrangement*.—Rosette.

*Shape*.—Broadly ovate.

*Number*.—About 150.

*Blade size*.—Grows to 15 cm long and 13.5 cm wide.

*Venation*.—Palmate.

*Lobing/division*.—7 shallow palmate lobes.

*Margins*.—Broadly crenate, undulation slight.

*Apex*.—Mucronulate.

*Base*.—Cordate, usually overlapping.

*Surface texture*.—Sparsely glandular-puberulent on both sides, semi-glossy.

*Leaf rugosity*.—Absent.

*Leaf undulation*.—Weak to medium.

*Petiole description*.—Grows to 20 cm long and 4 mm wide, glandular hairs, Greyed Purple 187A.

*Leaf color*.—New leaves; top side between Greyed Orange 166A and Greyed Red 178A with veins closest to Greyed Orange 166B, bottom side closest to Greyed Purple N186C with veins Greyed Purple 187B, old leaves; top side closest to Greyed Purple N186A with veins Greyed Red 180D, bottom side Greyed Purple 187A with veins Greyed Purple N187B.

Inflorescence:

*Size*.—Grows to 7 cm wide and 21 cm long.

*Type*.—Upright thyrse.

*Number of flowers per thyrse*.—About 70.

*Flower density*.—Light.

*Number of thyrse*.—About 10.

*Peduncle*.—Grows to 45 cm long and 3.5 mm wide at base, glandular hairs, Greyed Purple 187A.

*Pedicel*.—Grows to 2.5 mm long, 5 mm wide, with glandular hairs, Greyed Purple 187A.

*Bloom period*.—Late April to July in Canby, Oreg.

Flower bud:

*Size*.—3.5 mm wide and 5 mm long.

*Description*.—Glandular puberulent, ovoid, down facing.

*Color*.—Greyed Purple 186A on bottom ⅓ blending to Greyed Purple 186C on top ⅔.

Flower:

*Type*.—Perfect.

*Shape*.—Campanulate.

*Lastingness*.—30 to 45 days.

*Attitude*.—Side and down-facing.

*Size*.—5 mm long and 4 mm wide.

*Corolla description*.—5 petals, each 3 mm long, 1 mm wide at base for 1 mm, expanding to 2 mm wide near tip for 2 mm, margins entire, tip acute, glandular-puberulent on back side, glabrous on the inside, Red Purple 69D on both sides.

*Calyx description*.—Campanulate, 5 mm long and 4 mm wide, with 5 lobes with sinuses divided ½ way to the base, each 2 mm wide and 2.5 mm long, oblong in shape, back side glandular-puberulent, glabrous inside, tip obtuse, margin entire, outside color Greyed Purple 186A on bottom ½ blending to Greyed Purple 186C on top ½, inside Greyed Purple 186C.

*Stamen description*.—5 in number, filaments 1.5 mm long, Greyed Purple 186C, anthers 0.7 mm long, Greyed Orange 168A, pollen none.

*Pistil description*.—1, 2-beaked, 4.5 mm long and 2 mm wide, ovary 2 mm long and 2 mm wide, Green Yellow 1C, style 2 mm long, Green Yellow 1C, stigma bulbous in shape, 0.5 mm in diameter, closest to White 155C.

*Fragrance*.—None.

*Lastingness*.—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant substantially illustrated and described herein.

* * * * *